United States Patent [19]
Loria

[11] Patent Number: 5,912,240
[45] Date of Patent: Jun. 15, 1999

[54] 5-ANDROSTENE 3β, 17α DIOL AS AN INHIBITOR OF TUMOR GROWTH

[76] Inventor: Roger M. Loria, 3219 Brook Rd., Richmond, Va. 23227

[21] Appl. No.: 08/838,823

[22] Filed: Apr. 10, 1997

[51] Int. Cl.⁶ .................................................. A61K 31/56
[52] U.S. Cl. .............................................................. 514/182
[58] Field of Search ............................................... 514/182

*Primary Examiner*—Jerome D. Goldberg
*Attorney, Agent, or Firm*—Glenna Hendricks; Stephen Gates

[57] ABSTRACT

This invention relates to the field of pharmaceuticals for tumor-inhibitory effects. The 5-androstene 3β, 17α diol (αAED), its esters and ethers, are taught herein to achieve tumor-inhibiting effect.

13 Claims, No Drawings

5-ANDROSTENE 3β, 17α DIOL AS AN INHIBITOR OF TUMOR GROWTH

BACKGROUND OF THE INVENTION

1. Field of the Invention

This invention relates to the field of pharmaceuticals for tumor-inhibitory effects. The 5-androstene 3β,17α diol (αAED), its esters and ethers, are taught herein to achieve tumor-inhibiting effect.

2. Description of Related Art

Mifepristone (RU486) is used as a progesterone receptor antagonist (See U.S. Pat. No. 4,386,085, which is incorporated herein by reference in its entirety) and has been shown to have use both as an abortifacient and has been found useful for treating steroid-dependent breast cancer.

Flutamide, which has been disclosed in U.S. Pat. No. 3,847,988 (which is incorporated herein by reference in its entirety) is an antiandrogen that has been used to treat prostatic cancer, usually in conjunction with estrogen.

U.S. Pat. No. 2,521,586 to Levy, et al., teaches production of the 17-monobenzoate ester of androstene diol. No use of the 5-androstene 3β, 17α diol (αAED) is taught therein.

Peat, in U.S. Pat. No. 4,628,052 teaches a genus which might, arguably, within the scope of the genus, encompass the αAED. However, all examples and all named compounds require a keto group. Hence, it is reasonable to conclude that the αAED is not intended therein.

Tindall, in U.S. Pat. No. 2,845,381 teaches cosmetic compositions containing the αAED. No medicinal compositions appropriate for internal use or medicinal uses are suggested therein.

U.S. Pat. No. 4,882,322 to Johnson, et al. Teaches substituted 5-androstene 3β,17β diol to regulate or inhibit the conversion of androgens to estrogens. The αAED is not taught therein.

Swartz, et al., in U.S. Pat. No. 4,898,694 teaches a very large group of compounds which encompass substituted androstenediols. However, Schwartz does not suggest the αAED nor the esters and ethers claimed herein for any purpose.

Loria, in U.S. Pat. Nos. 5,206,008, 5,277,907, 5,3876,583, 5,461,042 and 5,478,566 teaches that the 5-androstene 3β,17β diol (βAED) and 5,-androstene 3β,7β,17β triol (AET) enhance immune response, and also are useful for counteracting the untoward effects of irradiation and chemotherapy, and buffer the anti-proliferative effects of hydrocortisone. None of these patents teaches or suggests use of αAED. As taught therein, the βAED is most effective if administered in such a manner that it contacts tissue of ectodermal origin.

SUMMARY OF THE INVENTION

The instant invention provides a means of accelerating cell aging and programed cell death in tumor cells. The practice of the invention involves administration of 3β,17α androstenetriol (which may be referred to in this application as either 17αAED or simply αAED) and esters and ethers thereof.

DESCRIPTION OF THE INVENTION

The instant invention relates to the use of 5-androstene 3β,17α diol (herein referred to as αAED or 17 αAED), its esters and ethers, to inhibit growth and accelerate cell aging, induce apoptosis and death of tumor cells as a means of treating malignancies. The active agents of the invention may also be used as contraceptives and abortifacients. The active agents are of the structure:

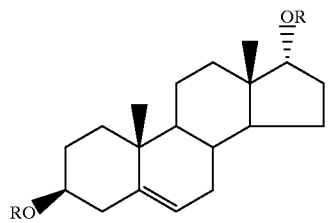

wherein R may be H, alkenyl of 2–8 carbons, alkyl of 1–8 carbons, phenylalkyl of 1–4 carbons, phenyl or $COR_2$, wherein $R_2$ is H; alkyl of 1–8 carbons, alkenyl of 2–8 carbons, phenylalkyl wherein the alkyl has 1–4 carbons (including benzyl) or phenyl. Any phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized.

It has been found that these active agents, when administered as described herein, inhibit cell growth. The αAED is administered in sufficient dosages to provide a blood concentration of from 5 to 10,000 ηM when given systemically. A more preferred blood or tissue fluid concentration is in the rang of 10 to 10,000 ηM. The dosage will vary with the type of cell to be inhibited. The method of administration will depend on the location of the target cells. Such means as parenteral or oral administration are also appropriate. The αAED may also be administered by applicator or in a spray to tissue during surgery. Compositions containing the active agents taught herein may be administered vaginally or rectally either by instillation of a liquid composition or on supports such as sponges.

Other preferred methods of administration include buccal, sublingual, nasal or endotracheal routes. Sprays or mists may be useful for such administration. Furthermore, sprays may be useful for administration to the operative area during surgery. For example, sprays may be used to contact the peritoneal cavity or the thoracic cavity during surgery.

Compositions of the invention may also be administered to the intestinal mucosa by oral or rectal routes. Suppositories, solutions for use as retention enemas and creams or jellies are appropriate means for use in rectal administration.

Compositions of the invention may also be applied to the vaginal mucosa using creams, jellies suppositories or douching solutions. The compositions may be in the form of prophylactic vaginal preparations or may be used in lubricants on condoms. Jellies and creams may also be administered by application in a cervical diaphragm which, when in place, will provide for prolonged contact with the cervix.

For purposes of administration into an orifice of the body, the compositions of the invention may be administered via a flexible tube into the target site. As indicated previously, the compositions containing αAED may be administered as a douche or retention enema. Other target sites include the bladder, uterus, trachea, nasopharynx, sinus or (via the nasal passage) the pituitary.

The carrier system used in a given instance will depend on the mode of administration. The active agents are lipophilic compounds. Solvents and carriers for lipophilic steroids known in the art are appropriate for use in the compositions containing αAED or the esters and ethers of αAED. Examples of such carriers are glycols such as polypropylene glycol, polyethylene glycol, ethanol, DMSO and cyclodextrins (especially the amorphous cyclodextrins). Cyclodextrins will pass through the buccal mucosa into the circulation easily. This method is particularly appropriate for administration as a means of avoiding intravenous administration while bypassing the liver. Other vehicles that should be considered include fatty acid esters of polyoxyethylene sorbital (Tweens) or sorbitan (Spans) for preparation of emulsions.

The compositions taught herein may be used to treat most neoplasms, including for, for example, use in treatment of neoplasms, including those of the blood-forming organs, the liver, pancreas, thyroid, andrenals, pituitary, ovaries, testicles, breast, central nervous system (including brain, spinal column), bone, connective tissue, lungs, liver, the gastrointestinal system, connective tissue, uterus, mucous membranes, mouth and tongue, the lining of the peritoneum, the lymphatics and sensory organs.

MATERIALS AND METHODS

The βAED, 17 beta-oestradiol and tamoxifen were obtained from Sigma Chemical Company (St. Louis, Mo.). The αAED and Flutamide were obtained from Steriloid, Inc. (Walton, N.H.) and Schering Corporation (Kenilworth, N.J.), respectively. All steroids except βAED were dissolved in ethanol. βAED was dissolved in DMSO:ETHOL (1:1 v/v). Stock solutions were filtered and kept at 4° C. For testing, stock solutions were diluted in media immediately before use. The final concentration of vehicle was always $\leq 0.2\%$ in all samples, and this concentration had no significant cytotoxic effect on the human breast cell cancer cell line designated ZR-75-1 (American Type Culture Collection) as determined by trypan blue exclusion.

The ZR-75-1 cell line (passage 89) was obtained from the American Type Culture Collection (Rockville, Md.). The cells were cultured in RPMI-1640 medium containing 10% heat-inactivated fetal calf serum, 200 $\mu$M L-glutamine, 10 NM HEPES, 1.5 U/ml penicillin, and 1.5 $\mu$g/ml streptomycin in 5% $CO_2$ at 37° C. The cells were passaged twice weekly.

Cell Growth for testing:

Cells were first seeded at initial density of $1 \times 10^5$ cells per ml in quadruplicates in 24 multi-well flat bottom plates (Costar). Cells were then allowed to adhere and grow in phenol red-free RPMI 64 media supplemented with 10% heat-inactivated fetal calf serum (FCS), 200 $\mu$M L-glutamine, 10 mM HEPES, 2.5 U/ml penicillin and 2.5 $\mu$g/ml streptomycin in 5% $CO_2$ at 37° C. After 48 hours, four wells were sacrificed and counted to determine plating efficiency. In the remaining wells, medium was removed by aspiration and cells in each well were exposed to the media containing the specified steroid. The controls containing only medium or medium with vehicle were also prepared. In all samples, medium was changed every 48 hours. At the pre-established time-point. Cells were removed by trypsinization and washed. Cell number and viability were determined by trypan blue exclusion using a hemocytometer. Parallel cultures were also run to determine cell proliferation.

Cell Proliferation Assays:

For cell proliferation assays, cell suspensions were prepared by trypsinization of cells from cultures prepared in accord with methods described above. Cell viability was determined by trypan blue exclusion. The cells were then seeded in flat-bottom 96-well microtiter plates at a density of $2 \times 10^3$ cells/well and were allowed to rest for 48 hours in order to adhere. Non-adherent dead cells were removed by aspiration. Cells were then grown in media without phenol red. Some of the media contained supplements as indicated above. The active agents or vehicle control were added to the media. The cells were then grown for six days. Media was changed on the samples every 48 hours. On day 6, cells were pulsed with 1 $\mu$Ci[$^3$J]-thymidine for the last 6 hours of incubation before harvesting onto glass filter using a HPD cell harvester (Cambridge Technology, Watertown, Mass.) and counted on a KLB scintillation counter.

Initial tests were carried out to determine the optimal (maximal) dose of αAED required to inhibit growth of the ZR-75-1 cells in in vitro as determined by tritiated tymidine incorporation. It was found that treatment of ZR-75-1 cells with αAED at doses ranging from 3.13 ηM to 50 ηM lead to a biphasic effect on the growth of ZR-71-1 cells when compared to vehicle control after 6 days. The αAED stimulated proliferation of ZR-75-1 cells at concentrations between 6.25 and 12.5 ηM ($P<0.01$) when compared with the vehicle control. At concentration of 25 ηM or greater, the αAED significantly inhibited the growth of ZR-75-1 cells, and this anti-proliferative effect occurred in a dose and time-dependent manner at half-maximal (50 ηM) and maximal dose (100 ηM) levels. To ensure that inhibition was not due to cytotoxicity, cell count and viability were assessed by trypan blue exclusion. The addition of the 17αAED was not toxic to the cells. As opposed to αAED, the βAED alone at 100 ηM concentrations did not have any antiproliferative effect on the growth of the ZR-75-1 cells.

EXAMPLE 1

ZR-75-1 cells ($2 \times 10^3$) were treated as described above over a six day period with differing concentrations of αAED or with vehicle-only cultures. The medium was changed every 48 hours. Cells were pulsed with $^3$H-thymidine for the last six hours of incubation.

Results showed increasing proliferation at 6.25 ηM with decreasing cell proliferation at 25 ηM and marked decrease at concentrations of 50 ηM concentrations.

EXAMPLE 2

Cells were treated as in Example 1, except that in some samples a combination of 17αAED and βAED were used. The concentration of the αAED varied while the concentration of the βAED in the samples containing the combination of agents remained constant at 2.5 ηM. Cells were pulsed with $^3$H-thymidine for the last six hours.

The proliferation of cells in cultures containing αAED in the presence of βAED showed decreased proliferation at all concentrations of αAED.

EXAMPLE 3

Effects of αAED on growth of ZR-75-1 cells in the presence of estradiol was studied. Cells treated with increasing concentration of αAED in the presence or absence of 1 ηM concentration of estradiol over a 6 day period were studied. Cells were treated with increasing concentration of αAED in the presence if 1 ηM concentration of estradiol over a 6 day period, with medium changed every 48 hours. Cells were pulsed with $^3$H-thymidine for the last six hours of incubation. At higher doses of αAED the αAED suppressed proliferation even in the presence of estradiol. Hence, estradiol can not effectively overcome the antiproliferative activity of αAED on this human breast cancer cell line.

EXAMPLE 4

Effects of αAED on growth of ZR-75-1 cells in the presence of Flutamide, an antiandrogen, were studied using the process of Example 3 except that estradiol was replaced with Flutamide. At concentrations of $\geq 6.25$ ηM concentrations of αAED, the antiproliferative effects were greatly enhanced in the presence of Flutamide. Hence, Flutamide appears to act synergistically with αAED to produce antiproliferative effects. Hence, the administration of αAED with antiandrogens, especially in treating estrogen-dependent malignancies such as breast cancer, should be considered particularly advantageous treatment option.

EXAMPLE 5

Example 5 was again studied in the presence of RU486. Again, it was shown that at effective concentrations it was possible to lower dosage of RU486 in the presence of effective amounts of 0.1 μl concentrations of αAED with 0.5 μM concentration of RU486 there was synergistic action to decrease proliferation of cells. This synergism was shown to be even greater at RU486 concentrations of 1 μM. This combination of active agents would be especially useful for treatment of tumors which are dependent on estrogen or progestrone

EXAMPLE 6

Preparation for instillation:

| Ingredient | % w/w |
| --- | --- |
| αAED | 0.01% |
| polypropylene glycol | 13.0% |
| Water | 86.5% |

EXAMPLE 7

Preparation for intravenous injection:

| Ingredient | Amount |
| --- | --- |
| αAED | 1 mg. |
| Ethanol | 5 ml. |
| Phosphate buffered saline | Add to 1000 ml. |

EXAMPLE 8

Effect of αAED on growth of lymphoid neoplasm (P388D1 cells obtained from the American Type Culture Collection) in the presence of RU486 at concentration of 0.5 μM and 1.0 μM was studied in accord with the methods described above. It was found that the use of αAED in combination with RU486 resulted in increased effectiveness over use of one agent.

EXAMPLE 9

Effects of αAED at doses of 50 ηM and 100 ηM doses on murine macrophage myeloma cells (RAW 264.7, obtained from the American Type Culture Collection) was studied. At both 50 ηM and 100 ηM levels there was significant inhibition of proliferation.

EXAMPLE 10

Preparation for instillation into the bladder for treatment of bladder cancer:

| Ingredient | Amount |
| --- | --- |
| αAED | 10 mg |
| DMSO | 100 ml |
| half-normal saline | 900 ml. |

EXAMPLE 11

Water, 100 ml, is mixed with 7 g. β-hydroxypropyl cyclodextrin and 1 mg αAED. Fill ampules with the solution and sterilize. This preparation may be added to solutions for administration to the mucosa, for oral administration, or for parenteral administration.

EXAMPLE 12

The cyclodextrin/αAED preparation is prepared as above. The material is freeze-dried and placed in sterile ampules. The resulting powder may be placed in vials. The contents of the vials may then be snorted into the nasal cavity. It is also appropriate to dissolve the contents of the vials and place in solution for intravenous or topical application, including for infusion into a wound site. It may also be applied by spraying or sponging into the operative site such as the abdominal or thoracic cavity.

EXAMPLE 13

The preparation of Example 12 is diluted with 100 ml water. The preparation is sprayed into the abdominal cavity during and after removal of a colon malignancy.

αAED may be delivered to or through the skin by any means, including subcutaneous or intradermal injection or topical application. One means of topical application is the use of skin patches impregnated with the active agent. This means of delivery is advantageous since it is non-invasive and easily administered by relatively unskilled care providers.

EXAMPLE 14

Capsules of a formulation of αAED for oral administration is prepared by mixing 2 mg. αAED, 15 mg. Starch and 5 mg. Magnesium stearate. The capsules are administered twice a day to achieve a daily dosage of 1–50 mg./da.

The compositions of the invention may be administered intrathecally either at the spinal level or into the cisterna magna.

When αAED, its esters or ethers are administered orally, it is necessary that the active agents be protected from destruction and absorption in the upper gastrointestinal tract. The active agents are most effective when the period of exposure to the mucosa of the intestinal tract is increased. Hence use of capsules containing the active agents in formulations that effect slow release in the intestine are appropriate.

The active agents may also be used in veterinary medicine for treatment of animals suffering from tumors. For purposes of such treatment, the αAED may be added to the chow of the animals.

The sterile solutions may be administered to the lung either by bronchioscopic means or by mist which may be under pressure.

Patched for administration of αAED may be formulated as adhesive patches containing the active agent. For example, the patch may be a discoid in which a pressure-sensitive silicone adhesive matrix containing the active agent may be covered with a non-permeable backing. The discoid may either contain the active agent in the adhesive or may be attached to a support made of material such as polyurethan foam or gauze that will hold the active agent. When patches are used in treating animals, the area must be shaved or plucked. In all instances, the area to which the patch is applied should be cleaned carefully before application.

EXAMPLE 15

A patch composed of trilaminate of an adhesive matrix sandwiched between a non-permeable backing and a protective covering layer is prepared in the following manner:

To a pressure-sensitive silicone adhesive composition BIOPSA™ q7-2920 (Dow Corning Corporation, Midland, Mich., U.S.A.) In cyclohexane (50% w/v) is added sufficient αAED to provide a 0.5% αAED composition. The adhesive is applied to a polyester film to provide in successive layers about 2 mg. Of active agent per cm². Patches should be covered with a protective layer which will be removed before application.

Patches may be prepared containing permeation enhancers such as cyclodextrin, butylated hydroxyanisole, or butylated hydroxytoluene.

The active agents may be administered to the mucosa of oral, pharyngeal or nasal cavity by tablet or lozenge.

The antiproliferative agents taught herein may be used in conjunction with other active agents such as vinca alkaloids, nucleic acid inhibitors, platinum agents, interleukin-2, interferons, alkylating agents, antimetabolites, corticosteroids, DNA intercalating agents, anthracyclines and ureas. Examples of specific agents, in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

What we claim is:

1. A method of inhibiting tumor cell proliferation by administration of a tumor proliferation inhibiting effective amount of at least one tumor-inhibiting agent which is αAED or an ester or ether thereof of the formula:

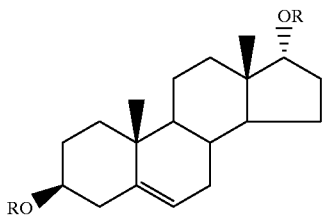

wherein either R may be H, alkenyl of 2–8 carbons, alkyl of 1–8 carbons, phenylalkyl wherein the alkyl chain is of 1–4 carbons, phenyl, $COR_2$, wherein $R_2$ is H, alkyl of 1–8 carbons, alkenyl of 2–8 carbons, phenylalkyl wherein the alkyl chain is of 1–4 carbons, or phenyl, and wherein any phenyl moiety may have up to three substituents chosen from among hydroxy, carboxy of 1–4 carbons, halo, alkoxy of 1–4 carbons, alkyl of 1–4 carbons or alkenyl of 2–4 carbons and wherein any alkyl may be a straight chain, a branched chain or the alkyl may be wholly or partially cyclized, wherein the tumor is sensitive to the compounds above.

2. A method of claim 1 wherein the active agent is administered orally.

3. A method of claim 1 wherein the active agent is administered parenterally.

4. A method of claim 1 wherein the active agent is administered orally.

5. A method of claim 1 wherein the active agent is applied to mucosal tissue.

6. A method of claim 5 wherein the active agent is administered rectally.

7. A method of claim 5 wherein the active agent is administered vaginally.

8. A method of claim 1 wherein the active agent is applied as a spray or mist.

9. A method of claim 1 wherein the active agent is applied to the site of the tumor or tumor bed.

10. A method of claim 1 wherein the active agent is administered as a patch.

11. A sterile composition of matter comprising a tumor proliferation inhibiting effective amount of αAED or an ester or ether thereof of the formula:

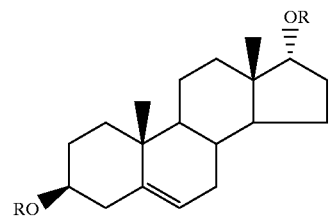

wherein R may be H, alkenyl of 2–8 carbons, alkyl of 1–8 carbons, phenylalkyl of 1–4 carbons, phenyl or $COR_2$, wherein $R_2$ is H; alkyl of 1–8 carbons, alkenyl of 2–8 carbons, phenylalkyl wherein the alkyl has 1–4 carbons (including benzyl) or phenyl, and any phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized, in a sterile solution appropriate for parenteral administration.

12. A composition of claim 11 in single dosage form in a container.

13. A composition of claim 11 in an isotonic solution.

* * * * *